(12) United States Patent
Ayalon

(10) Patent No.: US 11,574,710 B1
(45) Date of Patent: Feb. 7, 2023

(54) GRAPHICAL USER INTERFACE METHODOLOGIES FOR ALERTING A HEALTHCARE PRACTITIONER TO NEWLY DISPLAYED CLINICAL INFORMATION

(71) Applicant: Allscripts Software, LLC, Chicago, IL (US)

(72) Inventor: Yaniv Ayalon, Metzadot Yehuda (IL)

(73) Assignee: ALTERA DIGITAL HEALTH INC., Chicago, IL (US)

( * ) Notice: Subject to any disclaimer, the term of this patent is extended or adjusted under 35 U.S.C. 154(b) by 871 days.

(21) Appl. No.: 15/396,494

(22) Filed: Dec. 31, 2016

(51) Int. Cl.
*G16H 10/60* (2018.01)
*G16H 10/00* (2018.01)

(52) U.S. Cl.
CPC ............ *G16H 10/60* (2018.01); *G16H 10/00* (2018.01)

(58) Field of Classification Search
CPC ........ G06Q 50/22; G06Q 10/10; G06F 19/32; G06F 19/321
See application file for complete search history.

(56) References Cited

U.S. PATENT DOCUMENTS

| | | | | |
|---|---|---|---|---|
| 2006/0074633 | A1* | 4/2006 | Mahesh | G06F 19/321 704/9 |
| 2009/0217189 | A1* | 8/2009 | Martin | G16H 10/60 715/772 |
| 2014/0372147 | A1* | 12/2014 | White | G16Z 99/00 705/3 |
| 2016/0103963 | A1* | 4/2016 | Mishra | G16H 10/65 705/3 |
| 2017/0068785 | A1* | 3/2017 | Experton | H04W 12/02 |

* cited by examiner

*Primary Examiner* — Robert A Sorey
*Assistant Examiner* — Kristine K Rapillo
(74) *Attorney, Agent, or Firm* — Calfee, Halter & Griswold LLP

(57) ABSTRACT

A method includes accessing, by a healthcare practitioner via an EHR software application loaded on an electronic device, patient information for a patient; determining, by an agent application loaded on the electronic device, the patient for which the patient information was accessed; communicating, from the agent application to an agent service, a request for data regarding the patient; communicating, from the agent service to the agent application, accessed community data for the patient; displaying, in an interface of the agent application, one or more data items based on the accessed community data; receiving user input corresponding to toggling of the agent application from a filtered mode to an unfiltered mode; in response to the toggling, displaying additional data items coded visual indications that the respective data items are newly displayed, the coded visual indications being coded to indicate a reason why each respective data item was not previously displayed.

20 Claims, 15 Drawing Sheets

FIG. 8

Smith, Sally A.
Age: 31 | Sex F | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen, Pollinosis

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

---

Smith, Sally A.
31y | Female | 933145526

▽ Clinical Information
▷ Encounters
▷ Problems
   Leg Fracture
▷ Diagnoses
▷ Allergies
▷ Medications
▷ Measurements
▷ Labs
▷ Pathology
▷ Immunizations
▷ Imaging
▷ Procedures
▷ Documents Show All | Delta View EHR Agent

*FIG. 9*

Smith, Sally A.
31y | Female | 933145526

☐ ▽ Clinical Information
△ Encounters
▽ Problems
  Leg Fracture
  Type II Diabetes Mellitus
  Seasonal Affective Disorder
  High Blood Pressure
△ Diagnoses
△ Allergies
△ Medications
△ Measurements
△ Labs
△ Pathology
△ Immunizations EHR Agent Search Smith, Sally A.
Age: 31 | Sex F | MRN 933145526

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen, Pollinosis

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

*FIG. 10*

Smith, Sally A.
31y | Female | 933145526

▷ Clinical Information

△ Encounters
▽ Problems
  Leg Fracture
  Type II Diabetes Mellitus ⓘ
  Seasonal Affective Disorder
  High Blood Pressure ●
△ Diagnoses
△ Allergies
△ Medications
△ Measurements
△ Labs
△ Pathology
△ Immunizations EHR Agent

---

Smith, Sally A.
Age: 31 | Sex F | MRN 933145526

Search

Medical History

Active Problems
Type II Diabetes Mellitus (250.00) – w/o mention of complication or manifestation; type II, controlled
Managed by – SMITH, John MD | Onset Date – 16-May-2008
Hypertension (401.0) – Essential hypertension; malignant
Seasonal Allergic Reaction (477.0) – Allergic rhinitis, due to pollen, Pollinosis

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

*FIG. 12*

Smith, Sally A.
Age: 31 | Sex F | MRN 9[...]

Medical History

Active Problems
Type II Diabetes Mellitus (250.00) – w/o [...]
II, controlled
Managed by – SMITH, John MD | Onset
Hypertension (401.0) – Essential hyperte[...]
Seasonal Allergic Reaction (477.0) – Alle[...]

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

---

02-Jan-2013
Seasonal Affective Disorder
    Problem is from Facility that is
    specified to be filtered
Code:     825.12
Source Code:     825.12 (SAD)
My EHR Code:     n/a
Documented by:     Sue Prince, Ph.D.
Facility:     Friendly Facility
Source:     Just Note EHR

---

Smith, Sally A.
31y | Female | 933145526

Search

▽ Clinical Information
  △ Encounters
  ▽ Problems
    Leg Fracture
    Type II Diabetes Mellitus ⓘ
    Seasonal Affective Disorder ⓘ
    High Blood Pressure ⓘ
  △ Diagnoses
  △ Allergies
  △ Medications
  △ Measurements
  △ Labs
  △ Pathology
  △ Immunizations EHR Agent

*FIG. 14*

Smith, Sally A.
31y | Female | 933145526

🔍 Search

▽ Clinical Information
△ Encounters
▽ Problems
　Leg Fracture
　Type II Diabetes Mellitus ⓘ
　Seasonal Affective Disorder ☹
　High Blood Pressure ●
△ Diagnoses
△ Allergies
△ Medications
△ Measurements
△ Labs
△ Pathology
△ Immunizations EHR Agent

---

Smith, Sally A.
Age: 31 | Sex F | MRN 93...

Medical History

02-Jan-2013
High Blood Pressure

ⓘ Problem is semantically equivalent to a problem in your EHR.

Code:　　　　　401.0
Source Code:　　401.0 (HBP)
My EHR Code:　　401.0 (Hypertension)
Documented by: John Hue, M.D.
Facility:　　　　Heal U
Source:　　　　Wonderful EHR

Active Problems
Type II Diabetes Mellitus (250.00) – w/o ...
II, controlled
Managed by – SMITH, John MD | Onset ...
Hypertension (401.0) – Essential hyperten...
Seasonal Allergic Reaction (477.0) – Aller...

Current Medications
Accuretic 25-20 mg Oral Tablet; 1 PO QD
Metformin 1000 mg; 1 PO BID
Lantus 20 Units; qH S

Allergies
Cephalosporins
Eggs

Immunizations
Tetanous

Family History

Social History

GRAPHICAL USER INTERFACE METHODOLOGIES FOR ALERTING A HEALTHCARE PRACTITIONER TO NEWLY DISPLAYED CLINICAL INFORMATION

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to graphical user interface methodologies for alerting a healthcare practitioner user to newly displayed clinical information.

A need exists for improvement in graphical user interface methodologies for displaying clinical information. This need and other needs are addressed by one or more aspects of the present invention.

SUMMARY OF THE INVENTION

The present invention includes many aspects and features. Moreover, while many aspects and features relate to, and are described in, a particular context, the present invention is not limited to use only in this context, as will become apparent from the following summaries and detailed descriptions of aspects, features, and one or more embodiments of the present invention.

One aspect of the present invention relates to a method for providing a graphical user interface that alerts a healthcare practitioner user to newly displayed clinical information. The method includes, in response to accessing, by a healthcare practitioner via an electronic health records (EHR) software application loaded on an electronic device, patient information for a patient which effects display, in a first interface of the EHR software application, accessed patient information, determining, by an agent application loaded on the electronic device, context information for the EHR software application, including determining the patient for which the patient information was accessed. The method further includes communicating, from the agent application to an agent service, a request for data regarding the patient; communicating, from the agent service to the agent application, accessed community data for the patient; displaying, in a second interface of the agent application which overlays the first interface of the EHR software application, an indication of the patient, a plurality of categories for which patient information for the patient may be available, and one or more data items associated with a first category of the plurality of categories, the one or more data items being based on the accessed community data; receiving, at the electronic device via one or more input devices associated with the electronic device, user input corresponding to toggling of the agent application from a filtered mode to an unfiltered mode; in response to the received user input corresponding to toggling of the agent application from the filtered mode to the unfiltered mode, displaying, in the second interface of the agent application, one or more additional data items associated with the first category, and for each respective data item of the newly displayed one or more additional data items, a coded visual indication that the respective data item is newly displayed, the coded visual indication being coded to indicate a reason why the respective data item was not previously displayed in the filtered mode; receiving, at the electronic device via one or more input devices associated with the electronic device, user input corresponding to interaction with a first data item of the newly displayed one or more additional data items; and in response to the received user input corresponding to interaction with the first data item, displaying a message indicating why the first data item was not previously displayed in the filtered mode.

In a feature of this aspect, the electronic device comprises a desktop.

In a feature of this aspect, the electronic device comprises a laptop.

In a feature of this aspect, the electronic device comprises a touchscreen device.

In a feature of this aspect, the electronic device comprises a mobile device.

In a feature of this aspect, the electronic device comprises a tablet.

In a feature of this aspect, the electronic device comprises a phone.

In a feature of this aspect, the plurality of categories includes a category associated with diagnoses.

In a feature of this aspect, the plurality of categories includes a category associated with encounters.

In a feature of this aspect, the plurality of categories includes a category associated with problems.

In a feature of this aspect, the plurality of categories includes a category associated with allergies.

In a feature of this aspect, the plurality of categories includes a category associated with immunizations.

Another aspect relates to a method for providing a graphical user interface that alerts a healthcare practitioner user to newly displayed clinical information. The method includes, in response to accessing, by a healthcare practitioner via an electronic health records (EHR) software application loaded on an electronic device, patient information for a patient which effects display, in a first interface of the EHR software application, accessed patient information, determining, by an agent application loaded on the electronic device, context information for the EHR software application, including determining the patient for which the patient information was accessed. The method further includes communicating, from the agent application to an agent service, a request for data regarding the patient; communicating, from the agent service to the agent application, accessed community data for the patient; displaying, in a second interface of the agent application which overlays the first interface of the EHR software application, an indication of the patient, a plurality of categories for which patient information for the patient may be available, and one or more data items associated with a first category of the plurality of categories, the one or more data items being based on the accessed community data; receiving, at the electronic device via one or more input devices associated with the electronic device, user input corresponding to toggling of the agent application from a filtered mode to an unfiltered mode; and, in response to the received user input corresponding to toggling of the agent application from the filtered mode to the unfiltered mode, displaying, in the second interface of the agent application, one or more additional data items associated with the first category, and for each respective data item of the newly displayed one or more additional data items, a coded visual indication that the respective data item is newly displayed, the coded visual indication being coded to indicate a reason why the respective data item was not previously displayed in the filtered mode.

Another aspect relates to one or more computer readable media containing computer executable instructions for performing a disclosed method.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals.

FIG. 8 illustrates expansion of a "Problems" category of the EHR agent overlay interface of FIG. 7.

FIG. 9 illustrates toggling of the EHR agent from a "Delta View" mode to a "Show All" mode.

FIG. 10 illustrates display of additional problem items in a "Show All" mode.

FIG. 12 illustrates an interface of an EHR agent in accordance with one or more preferred implementations which includes a visual indication of items that are newly displayed in a "Show All" mode.

FIGS. 13-15 illustrate the display of informational messages indicating why particular problem items were previously filtered out in a "Delta View" mode.

DETAILED DESCRIPTION

Figure 1:
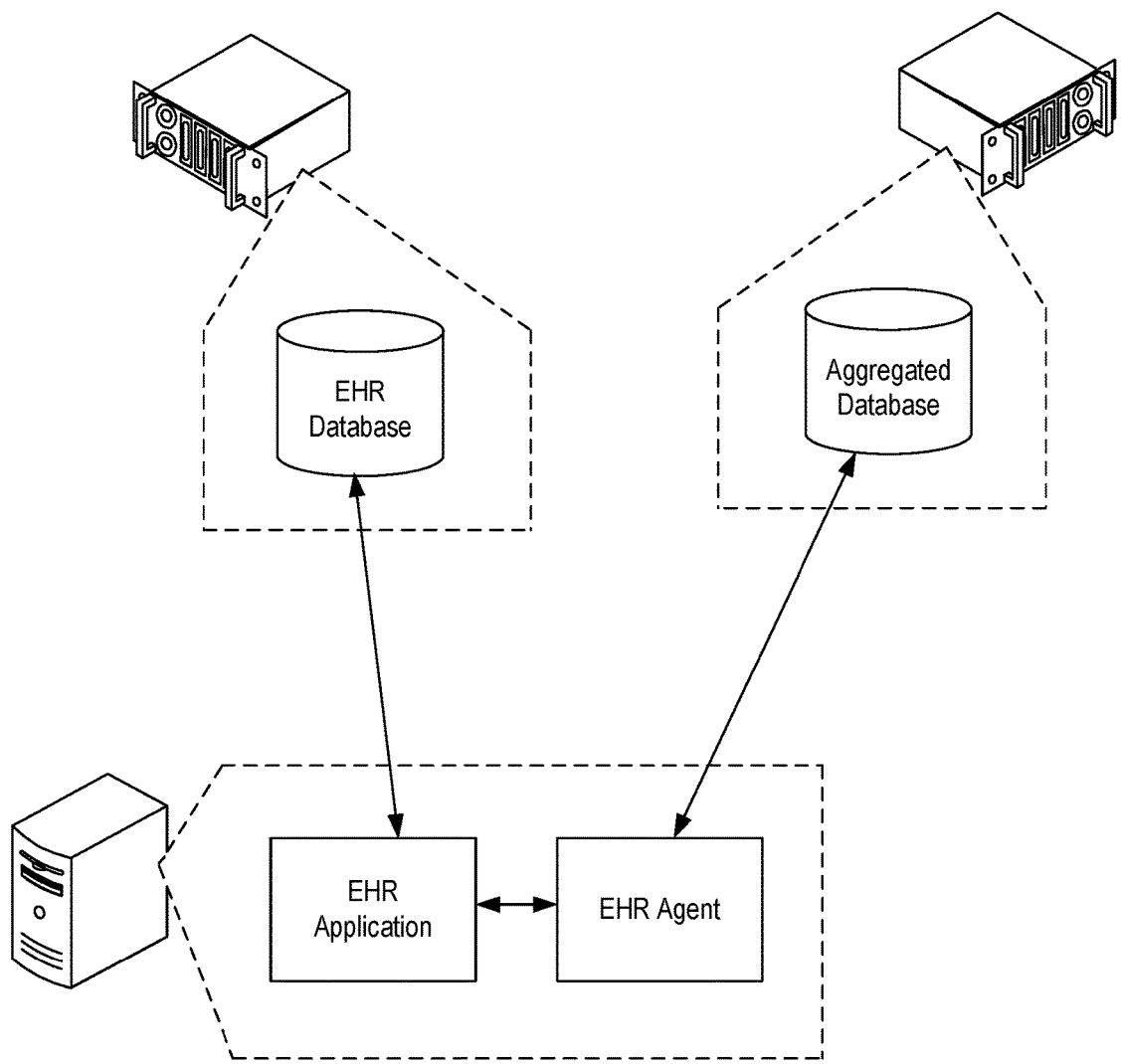
FIG. 1 illustrates an exemplary system in which a user device includes an EHR application and an EHR agent loaded thereon.

As a preliminary matter, it will readily be understood by one having ordinary skill in the relevant art ("Ordinary Artisan") that the invention has broad utility and application. Furthermore, any embodiment discussed and identified as being "preferred" is considered to be part of a best mode contemplated for carrying out the invention. Other embodiments also may be discussed for additional illustrative purposes in providing a full and enabling disclosure of the invention. Furthermore, an embodiment of the invention may incorporate only one or a plurality of the aspects of the invention disclosed herein; only one or a plurality of the features disclosed herein; or combination thereof. As such, many embodiments are implicitly disclosed herein and fall within the scope of what is regarded as the invention.

Accordingly, while the invention is described herein in detail in relation to one or more embodiments, it is to be understood that this disclosure is illustrative and exemplary of the invention, and is made merely for the purposes of providing a full and enabling disclosure of the invention. The detailed disclosure herein of one or more embodiments is not intended, nor is it to be construed, to limit the scope of patent protection afforded the invention in any claim of a patent issuing here from, which scope is to be defined by the claims and the equivalents thereof. It is not intended that the scope of patent protection afforded the invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the invention. Accordingly, it is intended that the scope of patent protection afforded the invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. 112, paragraph 6 or subsection (f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." When used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the invention are next described. The following description of one or more preferred embodiments is merely exemplary in nature and is in no way intended to limit the invention, its implementations, or uses.

In accordance with one or more preferred implementations, a system comprises an Electronic Healthcare Record (HER) agent, or Health Information Exchange (HIE) agent, which is designed to sit on top of existing EHR software in an EHR agnostic manner. Such a system is disclosed, for example, in U.S. Patent Application Pub. No. 2012/0215560, which patent application publication is hereby incorporated herein by reference. In accordance with one or more preferred implementations, a system aggregates data from a plurality of sources, including a plurality of EHR systems. In accordance with one or more preferred implementations, the system includes an EHR agent which comprises a graphical interface designed to overlay an EHR interface and provide information that may not be present in the EHR. The system preferably intercepts context from an EHR application (such as a current patient for which data is being displayed), and uses such intercepted context to select data for display in an agent interface.

In accordance with one or more preferred implementations, a system aggregates data from one or more sources, such as EHR systems or databases, patient portals, third party applications, payer systems and databases, and payer transaction processor systems. In accordance with one or more preferred implementations, a system stores aggregated information as community information, and aggregated community information is accessed by an EHR agent. Additionally or alternatively, in accordance with one or more preferred implementations, an EHR agent is configured to access information from multiple sources and aggregate information in real time at time of access.

Figure 2:
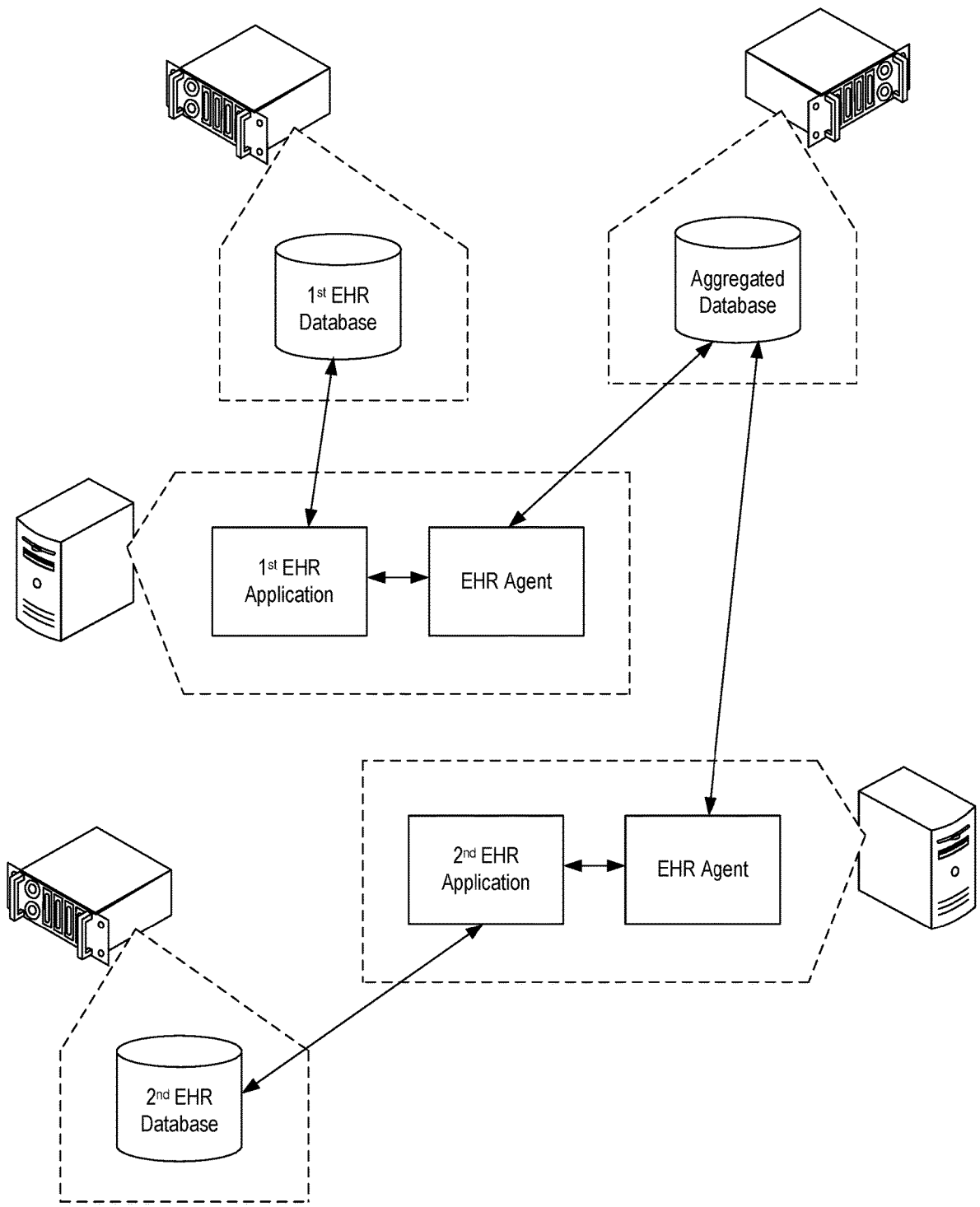
FIG. 2 illustrates a system with two user devices, each having a different EHR application loaded thereon.

FIG. 1 illustrates an exemplary system in which a user device includes an EHR application and an EHR agent loaded thereon. The EHR application is configured to access information from an EHR database associated with the application, while the EHR agent is configured to access community information from an aggregated database. FIG. 2 illustrates a similar system with two user devices, each having a different EHR application loaded thereon. Notably, although each EHR application accesses data from a different EHR database, each EHR agent accesses data from the same aggregated database.

Figure 3:
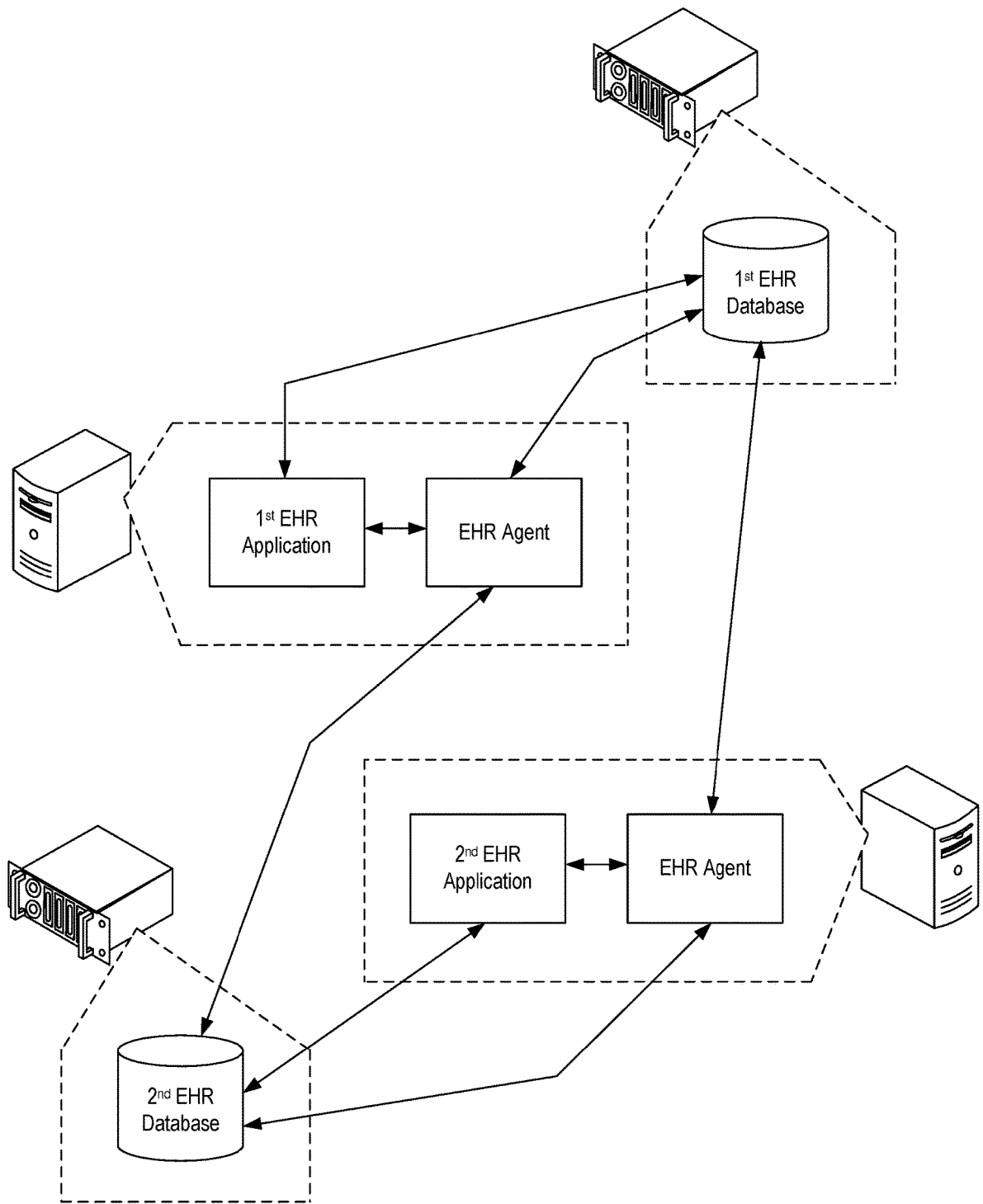
FIG. 3 illustrates another exemplary system in which EHR agents access information from multiple sources and aggregate information in real time at time of access.

FIG. 3 illustrates another exemplary system in which EHR agents access information from multiple sources and aggregate information in real time at time of access. Specifically, Like FIG. 2, FIG. 3 illustrates a system with two user devices, each having a different EHR application loaded thereon. The EHR agents illustrated in the exemplary system of FIG. 3, however, are configured to access information from both EHR databases.

Figure 4:
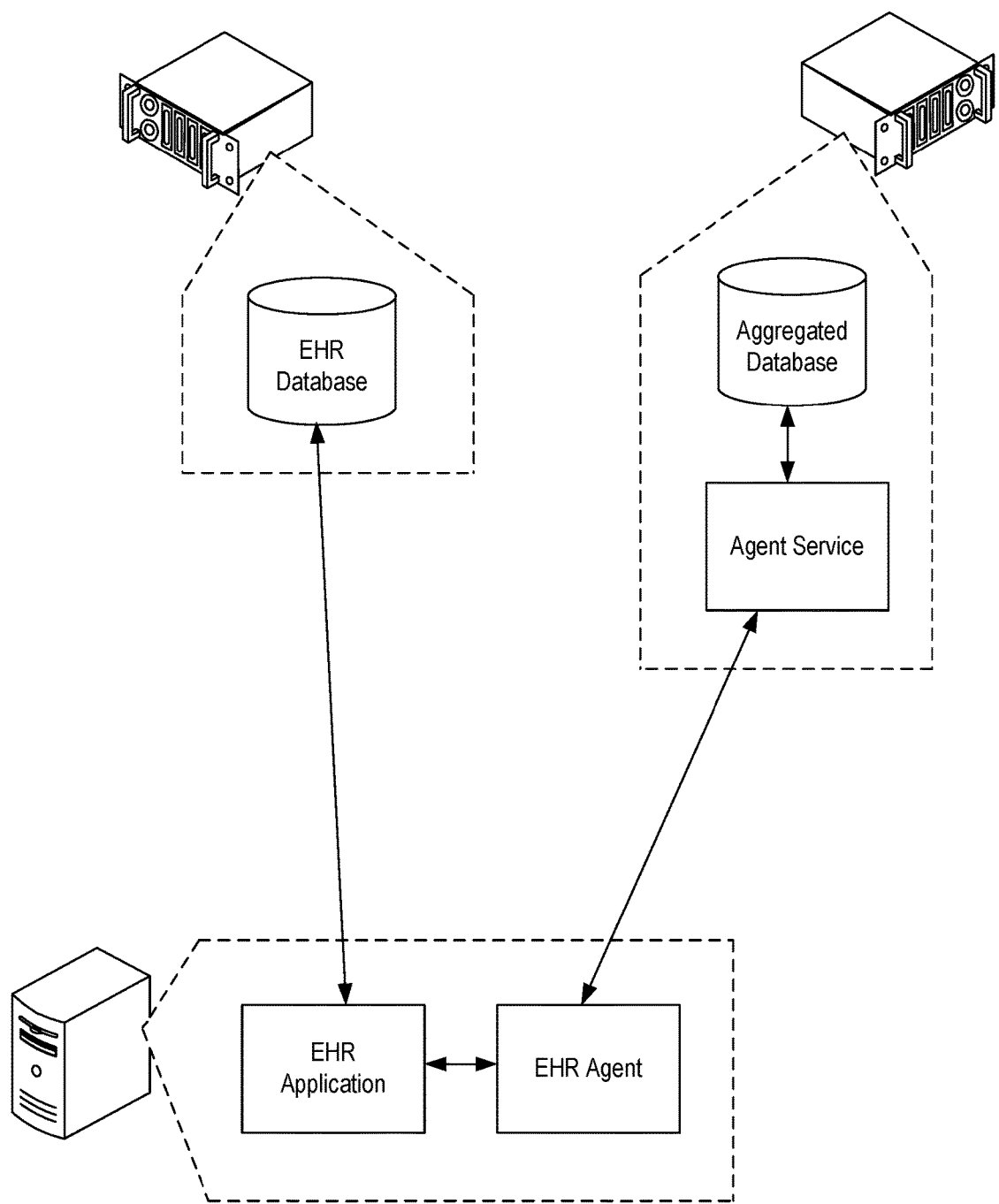
FIGS. 4 and 5 illustrate use of an agent service which may receive a request from an EHR agent, gather applicable information, and return a response.
Figure 5:
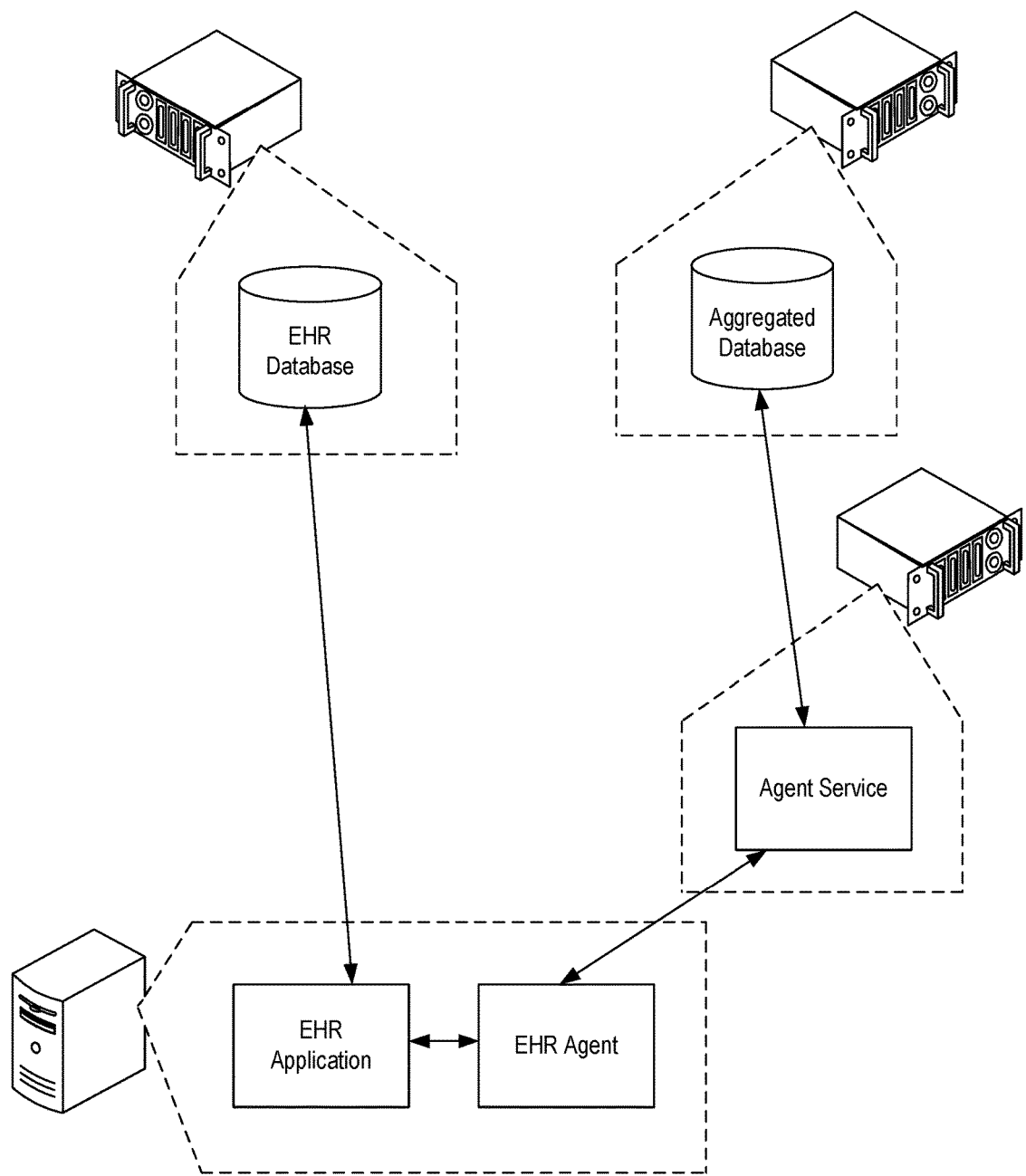

It will be appreciated that although FIG. 1 simply illustrates from a high level point of view an EHR agent accessing information from an aggregated database, a service may facilitate accessing of this information. For example, FIG. 4 illustrates use of an agent service which may receive a request from an EHR agent, gather applicable information, and return a response. One or more operations may be performed with or on accessed or returned information at the agent service and/or at the EHR agent. Such an EHR service may be located together with or remote from a database, as illustrated respectively in FIGS. 4 and 5. The EHR service and/or database may be cloud based.

Figure 6:
FIG. 6 illustrates an interface of an exemplary EHR application.
Figure 7:
FIG. 7 illustrates an EHR agent including an overlay interface which is displaying information for the patient.
Figure 11:
FIG. 11 illustrates the display of additional information for a particular problem item.

FIG. 6 illustrates an interface of an exemplary EHR application. The EHR application is displaying patient information for a patient loaded from an EHR database. FIG. 7 illustrates an EHR agent including an overlay interface which is displaying information for the patient. In particular, the EHR agent is displaying a plurality of expandable categories of health information for the patient. The EHR agent has intercepted context from the EHR application, and based on such intercepted context, is displaying information for the same patient as the EHR application. While the EHR application is only utilizing information loaded from the EHR database, the EHR agent is utilizing information from other sources as well.

Figure 8:
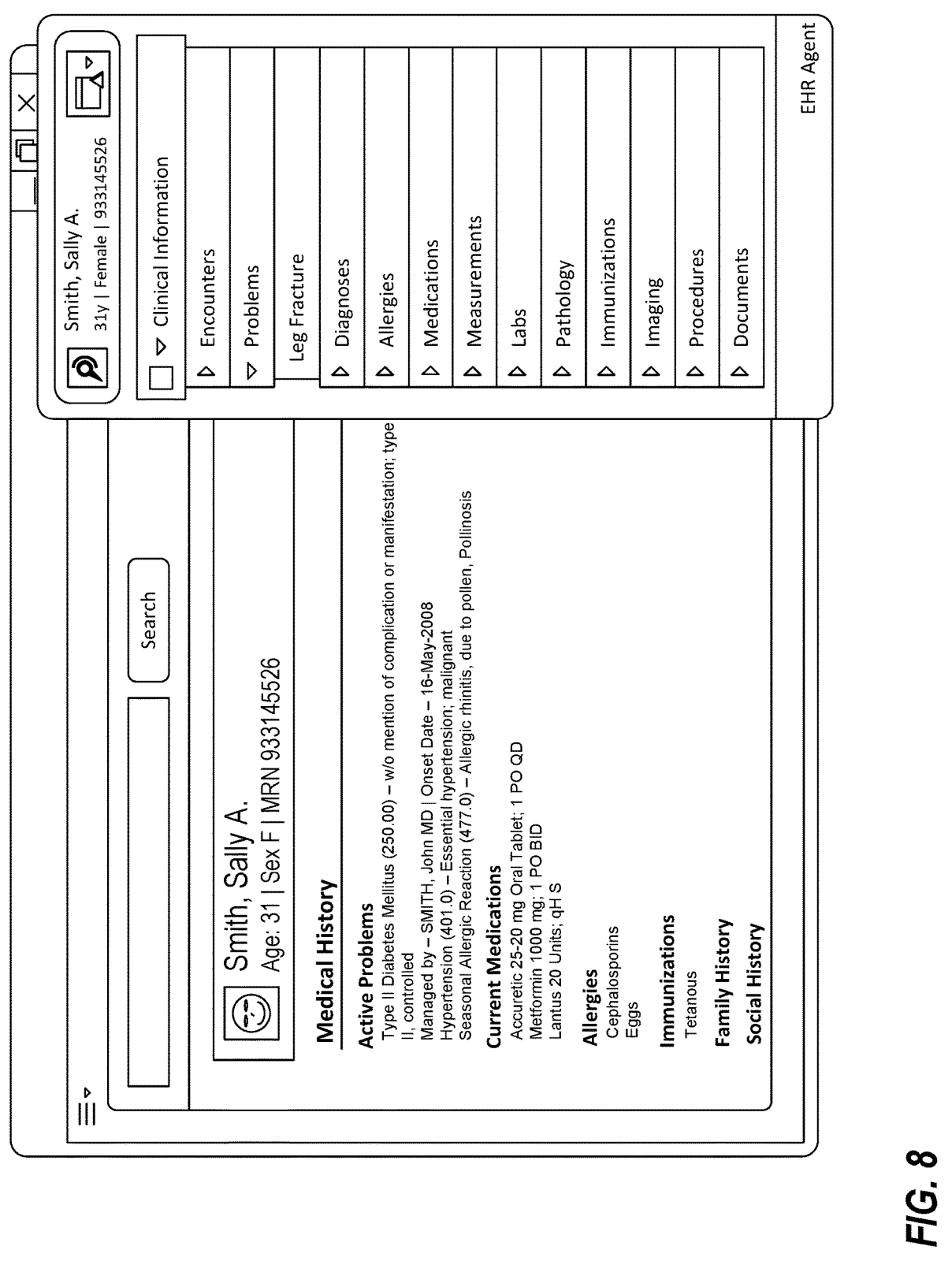

The displayed categories in the EHR agent for which additional information is available are expandable, as illustrated in FIG. 8, in which a "Problems" category has been expanded to reveal a "Leg Fracture" problem item.

Notably, it is possible that aggregated community information accessed and displayed by the EHR agent includes data from the native EHR application the user is currently using, or data that is equivalent to data in the native EHR application. In this case, the EHR agent might display data that is duplicative of data that is already displayed in the native EHR.

In order to try to address this issue, the EHR agent includes filtering functionality that allows a user indicate that he or she does not wish to have the EHR agent display all of the information it has accessed, and instead should only display a "Delta View" showing data that has been filtered (e.g. is believed to be distinct from data already present in the native EHR application the user is currently using).

The exemplary EHR agent that is illustrated includes filtering functionality for a "Delta View" that filters out data from display if it qualifies under one of three different filter criteria, although additional filter criteria and filters may be utilized in accordance with one or more preferred implementations.

First, the "Delta View" filters out community data items (e.g. problem items, medication items) that are determined to have originated from the native EHR application the user is using. For example, a community data item may be identified as a duplicate of a native data item if a source system ID for the items match, indicating they came from the same source system, and if a source system item ID for the items match, indicating that they had the same specific ID in that source system.

Additionally, the "Delta View" filters out community data items (e.g. problem data items, medication data items) that are determined to be a duplicate of a native data item already displayed in the native EHR application the user is using. A community data item may be identified as a duplicate of a native data item based on a semantic or other comparison of data for the two data items (e.g. a comparison of data values for the two items determines that the items have identical data values for all (or all relevant) data fields). For example, a community problem data item might be determined to be a duplicate of an existing native problem data item if the two items have the same ICD code and diagnosis date (although it will be appreciated that this is a simplistic example and additional comparisons may be utilized). As another example, in a medication data item context, a community medication data item might be determined to be a duplicate based on comparison of a medication name (with brand/trade names, generic names, and chemical names corresponding to one another potentially or optionally being considered to match), strength, dosage form, code (e.g. RxNorm code), status, and date.

Additionally still, the "Delta View" may filter out community data items that originated from a facility that a user has specifically requested to filter out. For example, a community data item may be filtered out if a facility identifier associated with the community data item matches a facility identifier included in a filter list.

Returning to FIG. 8, the EHR Agent is in a "Delta View" mode and displayed problems in the "Problems" category have been filtered, thus resulting in only the "Leg Fracture" problem item being displayed.

When the user switches from "Delta View" mode to a "Show All" mode, as illustrated in FIG. 9, additional problem items that were previously filtered out from display are displayed, as illustrated in FIG. 10.

In the illustrated example of FIGS. 9-10, it is relatively easy to discern which items are displayed in the "Show All" mode that were not displayed in the "Delta View", but it will be appreciated that if more items are displayed, especially if multiple categories are expanded, it can become very difficult to readily discern which items are newly displayed in the "Show All" mode that were not previously displayed in the "Delta View" mode.

Additionally, although there are multiple different filter criteria that might have caused a particular item to not be displayed in the "Delta View" mode, it can be difficult or even impossible for a user to discern why a particular item was not displayed in the "Delta View" mode. A user can interact with a problem item to display additional information and try to determine that a source of the problem item is the native EHR, or that a code for the problem item matches a code for an existing problem in the native EHR, but this can be time consuming and may not even work. Notably, the more filtering criteria utilized in a system, the more difficult it can become for a user to try to discern why an item may have been filtered out.

In accordance with one or more preferred implementations, an EHR agent is configured such that switching from a "Delta View" mode to a "Show All" mode effects display of a visual indication (e.g. icon) for each newly displayed item that was previously filtered out, as illustrated in FIG. 12. In accordance with one or more preferred implementations, the visual indication for an item is coded (e.g. color coded, such as green, yellow, etc.) to indicate why the item was filtered out in the "Delta View" mode. Further, in accordance with one or more preferred implementations, when a user interacts with a newly displayed problem item to display additional information for that problem item, an informational message is displayed explaining why the item was filtered out in the "Delta View" mode. In accordance with one or more preferred implementations, this informational message is coded (e.g. color coded) to match the coding of the visual indication associated with the problem item.

Figure 13:

For example, in FIG. 12, the newly displayed "Diabetes Mellitus Type II" problem item is color coded to indicate that it was previously filtered out because it was determined to have originated from the native EHR application the user is using. When the user interacts with this problem item and additional information is displayed, an informational message is displayed explaining why the item was filtered out in the "Delta View" mode, as illustrated in FIG. 13.

Similarly, in FIG. 12, the newly displayed "Seasonal Affective Disorder" problem item is color coded to indicate that it was previously filtered out because it was determined to have originated from a facility that has specifically been requested to be filtered out. When the user interacts with this problem item and additional information is displayed, an informational message is displayed explaining why the item was filtered out in the "Delta View" mode, as illustrated in FIG. 14.

Further, in FIG. 12, the newly displayed "High Blood Pressure" problem item is color coded to indicate that it was previously filtered out because it was determined to be a duplicate of a native problem item already displayed in the native EHR application. When the user interacts with this problem item and additional information is displayed, an informational message is displayed explaining why the item was filtered out in the "Delta View" mode, as illustrated in FIG. 15.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for providing a graphical user interface that alerts a healthcare practitioner to newly displayed clinical information, the method comprising:

determining, by an agent application loaded on an electronic device operated by the healthcare practitioner, an identifier for a patient for which patient information is being displayed within an interface of an electronic health records (EHR) software application also loaded on the electronic device, wherein the patient information is maintained by the EHR software application in an EHR database;

responsive to determining the identifier for the patient, communicating, from the agent application to an agent service executing on a server computing device, the identifier for the patient;

receiving, from the agent service and by the agent application and based upon the identifier for the patient, community data for the patient that is aggregated from a plurality of electronic sources, wherein each of the plurality of electronic sources maintain a respective subset of the community data for the patient;

responsive to receiving the community data for the patient, displaying, by the agent application and in an interface of the agent application which overlays the interface of the EHR software application and in a filtered mode of the agent application, an indication of the patient, a plurality of categories from the community data for the patient, and a data item that falls within a category in the plurality of categories, the data item being from the community data for the patient, wherein the data item is not included in the patient information being displayed by the EHR software application;

receiving, by the agent application via an input device associated with the electronic device, user input corresponding to toggling of the agent application from the filtered mode to an unfiltered mode;

responsive to receiving the user input corresponding to toggling of the agent application from the filtered mode to the unfiltered mode, displaying, by the agent application and in the interface of the agent application:
an additional data item that falls within the category, the additional data item being from the community data; and
an icon that indicates that the additional data item is newly displayed within the interface of the agent application, the icon being visually coded to indicate a reason why the additional data item was not previously displayed in the filtered mode of the agent application, wherein the reason is at least one of:
the additional data item originates from the EHR software application;
the additional data item is duplicative to the patient information being displayed within the interface of the EHR software application; or
the additional data item originates from an electronic source in the plurality of electronic sources that the healthcare practitioner has indicated is to be filtered out from display within the interface of the agent application;
receiving, by the agent application via the input device associated with the electronic device, user input corresponding to interaction with the additional data item displayed within the interface of the agent application; and
responsive to receiving the user input corresponding to interaction with the additional data item, displaying, by the agent application, a textual message indicating the reason why the additional data item was not previously displayed in the filtered mode within the interface of the agent application.

2. The method of claim 1, wherein the electronic device comprises a desktop.

3. The method of claim 1, wherein the electronic device comprises a laptop.

4. The method of claim 1, wherein the electronic device comprises a touchscreen device.

5. The method of claim 1, wherein the electronic device comprises a mobile device.

6. The method of claim 1, wherein the electronic device comprises a tablet.

7. The method of claim 1, wherein the electronic device comprises a phone.

8. The method of claim 1, wherein the plurality of categories includes a category associated with diagnoses.

9. The method of claim 1, wherein the plurality of categories includes a category associated with encounters.

10. The method of claim 1, wherein the plurality of categories includes a category associated with problems.

11. The method of claim 1, wherein the plurality of categories includes a category associated with allergies.

12. The method of claim 1, wherein the plurality of categories includes a category associated with immunizations.

13. A method for providing a graphical user interface that alerts a healthcare practitioner to newly displayed clinical information, the method comprising:
determining, by an agent application loaded on an electronic device operated by the healthcare practitioner, an identifier for a patient for which patient information is being displayed within an interface of an electronic health records (EHR) software application also loaded on the electronic device, wherein the patient information is maintained by the EHR software application in an EHR database;
responsive to determining the identifier for the patient, communicating, from the agent application to an agent service executing on a server computing device, the identifier for the patient;
receiving, from the agent service and by the agent application and based upon the identifier for the patient, community data for the patient that is aggregated from a plurality of electronic sources, wherein each of the plurality of electronic sources maintain a respective subset of the community data for the patient;
responsive to receiving the community data for the patient, displaying, by the agent application and in an interface of the agent application which overlays the interface of the EHR software application and in a filtered mode of the agent application, an indication of the patient, a plurality of categories from the community data for the patient, and a data item that falls within a category in the plurality of categories, the data item being from the community data for the patient, wherein the data item is not included in the patient information being displayed by the EHR software application;
receiving, by the agent application via an input device associated with the electronic device, user input corresponding to toggling of the agent application from the filtered mode to an unfiltered mode; and
responsive to receiving the user input corresponding to toggling of the agent application from the filtered mode to the unfiltered mode, displaying, by the agent application and in the interface of the agent application:
an additional data item that falls within the first category, the additional data item being from the community data; and
an icon that indicates that the additional data item is newly displayed within the interface of the agent application, the icon being visually coded to indicate a reason why the additional data item was not previously displayed in the filtered mode of the agent application, wherein the reason is at least one of:
the additional data item originates from the EHR software application;
the additional data item is duplicative to the patient information being displayed within the interface of the EHR software application; or
the additional data item originates from an electronic source in the plurality of electronic sources that the healthcare practitioner has indicated is to be filtered out from display within the interface of the agent application.

14. The method of claim 13, wherein the electronic device comprises a desktop.

15. The method of claim 13, wherein the electronic device comprises a laptop.

16. The method of claim 13, wherein the electronic device comprises a touchscreen device.

17. The method of claim 13, wherein the electronic device comprises a mobile device.

18. The method of claim 13, wherein the electronic device comprises a tablet.

19. The method of claim 13, wherein the electronic device comprises a phone.

20. A computer readable media containing computer executable instructions that when executed by a processor, cause the processor to perform acts comprising:

determining, by an agent application loaded on an electronic device, an identifier for a patient for which patient information is being displayed within an interface of an electronic health records (EHR) software application also loaded on the electronic device, wherein the patient information is maintained by the EHR software application in an EHR database;

responsive to determining the identifier for the patient, communicating, from the agent application to an agent service executing on a server computing device, the identifier for the patient;

receiving, from the agent service and by the agent application and based upon the identifier for the patient, community data for the patient that is aggregated from a plurality of electronic sources, wherein each of the plurality of electronic sources maintain a respective subset of the community data for the patient;

responsive to receiving the community data for the patient, displaying, by the agent application and in an interface of the agent application which overlays the interface of the EHR software application and in a filtered mode of the agent application, an indication of the patient, a plurality of categories from the community data for the patient, and a data item that falls within a category in the plurality of categories, the data item being from the community data, wherein the data item is not included in the patient information being displayed by the EHR software application;

receiving, by the agent application via an input device associated with the electronic device, user input corresponding to toggling of the agent application from the filtered mode to an unfiltered mode; and responsive to receiving the user input corresponding to toggling of the agent application from the filtered mode to the unfiltered mode, displaying, by the agent application and in the interface of the agent application:

an additional data item that falls within the category, the additional data item being from the community data; and an icon that indicates that the additional data item is newly displayed within the interface of the agent application, the icon being visually coded to indicate a reason why the additional data item was not previously displayed in the filtered mode of the agent application, wherein the reason is at least one of:

the additional data item originates from the EHR software application;

the additional data item is duplicative to the patient information being displayed within the interface of the EHR software application; or the additional data item originates from an electronic source in the plurality of electronic sources that a user has indicated is to be filtered out from display within the interface of the agent application.

* * * * *